US012778420B2

(12) United States Patent
Wen et al.

(10) Patent No.: US 12,778,420 B2
(45) Date of Patent: Nov. 3, 2026

(54) SYSTEMS AND METHODS FOR APPLANATION TONOMETRY AND TONOGRAPHY

(71) Applicant: Duke University, Durham, NC (US)

(72) Inventors: Joanne C. Wen, Durham, NC (US); Erin Simons, Cary, NC (US); Scott Liddle, Cary, NC (US)

(73) Assignee: Duke University, Durham, NC (US)

(*) Notice: Subject to any disclaimer, the term of this patent is extended or adjusted under 35 U.S.C. 154(b) by 274 days.

(21) Appl. No.: 18/684,622

(22) PCT Filed: Aug. 29, 2022

(86) PCT No.: PCT/US2022/041931
§ 371 (c)(1),
(2) Date: Feb. 16, 2024

(87) PCT Pub. No.: WO2023/028373
PCT Pub. Date: Mar. 2, 2023

(65) Prior Publication Data

US 2024/0350007 A1 Oct. 24, 2024

Related U.S. Application Data

(60) Provisional application No. 63/237,715, filed on Aug. 27, 2021.

(51) Int. Cl.
*A61B 5/00* (2006.01)
*A61B 3/14* (2006.01)
*A61B 3/16* (2006.01)

(52) U.S. Cl.
CPC .................................... *A61B 3/16* (2013.01); *A61B 3/14* (2013.01)

(58) Field of Classification Search
CPC .................................... A61B 3/16; A61B 3/14
See application file for complete search history.

(56) References Cited

U.S. PATENT DOCUMENTS 3,330,152 A 7/1967 Mackay
4,766,904 A * 8/1988 Kozin ...................... A61B 3/16 600/405

(Continued)

FOREIGN PATENT DOCUMENTS

AU 741461 B2 11/2001
BR 9711993 C1 8/2002

(Continued)

OTHER PUBLICATIONS

International Search Report and Written Opinion for Application No. PCT/US2022/041931 dated Dec. 19, 2022 (6) pages).

(Continued)

*Primary Examiner* — May A Abouelela
(74) *Attorney, Agent, or Firm* — Barnes & Thornburg LLP

(57) ABSTRACT

Systems, devices, and methods for measuring intraocular pressure of the eye are disclosed. More particularly, the improved systems, devices, and methods enable the use of applanation tonometry and tonography to make such measurements using a portable, handheld applanation device. The applanation devices apply a constant fixed force to the surface of the eye. The resulting applanation mire can be captured by an image-capturing device and the intraocular pressure can be calculated using a provided algorithm based on the applanation mire and a known reference with respect to the eye.

18 Claims, 7 Drawing Sheets

(56) References Cited

U.S. PATENT DOCUMENTS

| | | | | | |
|---|---|---|---|---|---|
| 4,987,899 | A * | 1/1991 | Brown | A61B 3/16 | |
| | | | | 600/405 | |
| 5,070,875 | A * | 12/1991 | Falck | A61B 3/16 | |
| | | | | 600/405 | |
| 5,355,884 | A * | 10/1994 | Bennett | A61B 3/16 | |
| | | | | 600/405 | |
| 5,540,227 | A * | 7/1996 | Poole | A61B 3/16 | |
| | | | | 600/404 | |
| 5,671,737 | A * | 9/1997 | Harosi | A61B 3/16 | |
| | | | | 600/398 | |
| 5,830,139 | A | 11/1998 | Abreu | | |
| 5,954,645 | A * | 9/1999 | Luce | A61B 3/165 | |
| | | | | 351/212 | |
| 6,083,160 | A | 7/2000 | Lipman | | |
| 6,817,981 | B2 * | 11/2004 | Luce | A61B 3/165 | |
| | | | | 600/399 | |
| 9,155,467 | B1 * | 10/2015 | Enikov | A61B 3/16 | |
| 2001/0051770 | A1 * | 12/2001 | Falck, Jr. | A61B 3/16 | |
| | | | | 600/398 | |
| 2002/0049389 | A1 * | 4/2002 | Abreu | A61B 3/0058 | |
| | | | | 600/318 | |
| 2002/0173712 | A1 * | 11/2002 | Feldon | A61B 3/16 | |
| | | | | 600/405 | |
| 2002/0177768 | A1 * | 11/2002 | Fleischman | A61B 3/16 | |
| | | | | 600/399 | |
| 2004/0044278 | A1 * | 3/2004 | O'Donnell, Jr. | A61B 3/16 | |
| | | | | 600/399 | |
| 2004/0210123 | A1 * | 10/2004 | Davidson | A61B 3/16 | |
| | | | | 600/398 | |
| 2004/0260168 | A1 * | 12/2004 | Shimmyo | A61B 3/16 | |
| | | | | 600/399 | |
| 2005/0020896 | A1 * | 1/2005 | Fuller | A61B 3/1005 | |
| | | | | 600/405 | |
| 2005/0143637 | A1 * | 6/2005 | Feldon | A61B 3/16 | |
| | | | | 600/405 | |
| 2009/0030300 | A1 * | 1/2009 | Ghaboussi | A61B 3/16 | |
| | | | | 600/405 | |
| 2009/0131779 | A1 | 5/2009 | Siegenthaler | | |
| 2011/0015512 | A1 | 1/2011 | Pan et al. | | |
| 2012/0108941 | A1 * | 5/2012 | Maggiano | A61B 3/10 | |
| | | | | 600/405 | |
| 2013/0144185 | A1 * | 6/2013 | Fuller | A61B 5/7278 | |
| | | | | 600/561 | |
| 2013/0211285 | A1 * | 8/2013 | Fuller | A61B 5/031 | |
| | | | | 600/561 | |
| 2014/0111774 | A1 * | 4/2014 | Komine | A61B 3/14 | |
| | | | | 351/221 | |
| 2014/0163352 | A1 | 6/2014 | Falck, Jr. et al. | | |
| 2015/0094560 | A1 * | 4/2015 | Cohen | A61B 3/16 | |
| | | | | 600/398 | |
| 2016/0029888 | A1 * | 2/2016 | Maggiano | A61B 3/0083 | |
| | | | | 600/405 | |
| 2017/0215728 | A1 * | 8/2017 | Wen | A61B 3/0025 | |
| 2018/0296090 | A1 * | 10/2018 | McCafferty | A61B 3/16 | |
| 2019/0350456 | A1 | 11/2019 | Koziol | | |
| 2021/0353145 | A1 * | 11/2021 | Kamthan | A61B 3/16 | |

FOREIGN PATENT DOCUMENTS

| | | | | | |
|---|---|---|---|---|---|
| CA | 2264193 | C | | 3/2008 | |
| CN | 1229345 | C | | 11/2005 | |
| EP | 0926979 | A1 | | 7/1999 | |
| IL | 128825 | A | | 7/2004 | |
| JP | 2005017231 | A | | 1/2005 | |
| JP | 2018517929 | A | * | 7/2018 | G02C 7/046 |
| JP | 2021515631 | A | * | 6/2021 | G01N 33/54366 |
| KR | 100411363 | B1 | | 12/2003 | |
| KR | 101153348 | B1 | * | 6/2012 | A61B 3/0016 |
| WO | 1998009564 | A1 | | 3/1998 | |
| WO | 2009111726 | A2 | | 9/2009 | |
| WO | WO-2011106799 | A2 | * | 9/2011 | A61B 3/16 |
| WO | WO-2014202840 | A1 | * | 12/2014 | A61B 3/0091 |
| WO | WO-2015074094 | A1 | * | 5/2015 | A61B 3/16 |
| WO | WO-2018065646 | A1 | * | 4/2018 | A61B 3/16 |
| WO | WO-2019118410 | A1 | * | 6/2019 | A61B 3/16 |
| WO | WO-2021034951 | A1 | * | 2/2021 | A61B 5/6898 |
| WO | 2023028373 | A1 | | 3/2023 | |

OTHER PUBLICATIONS

About us—iCare. https://www.icare-world.com/us/about-us/ (2020).

Al Ali, Alaa, Stephen Hallingham, and Yvonne M. Buys. "Workforce supply of eye care providers in Canada: optometrists, ophthalmologists, and subspecialty ophthalmologists." Canadian Journal of Ophthalmology 50.6 (2015): 422-428.

Aziz, K. & Friedman, D. S. Tonometers-which one should I use? Eye 32, 931-937 (2018).

Boassa, Daniela, W. Daniel Stamer, and Andrea J. Yool. "Ion channel function of aquaporin-1 natively expressed in choroid plexus." Journal of Neuroscience 26.30 (2006): 7811-7819.

Buchan, J. C., Macleod, D., Hickman, W. & Bastawrous, A. Systematic bias in real-world tonometry readings based on laterality? Eye 34, 360-365 (2020).

Cook, J. A. et al. Systematic review of the agreement of tonometers with Goldmann applanation tonometry. Ophthalmology 119, 1552-1557 (2012).

Covin, et al., The Societal Costs of Blindness from Uncontrolled Glaucoma. (Glaucoma Today 2014).

Dismuke, W. Michael, et al. "Concentration-related effects of nitric oxide and endothelin-1 on human trabecular meshwork cell contractility." Experimental eye research 120 (2014): 28-35.

Eye health statistics. https://www.aao.org/newsroom/eye-health-statistics.

Global Tonometers Market 2018-2022 | Growing Demand for Hand-Held Tonometers to Boost Growth | Technavio.

Hardy, Katharine M., et al. "Extracellular trafficking of myocilin in human trabecular meshwork cells." Journal of Biological Chemistry 280.32 (2005): 28917-28926.

Hoffman, Emely A., et al. "Regulation of myocilin-associated exosome release from human trabecular meshwork cells." Investigative ophthalmology & visual science 50.3 (2009): 1313-1318.

Icare Home Tonometer Remote Monitoring—Corcoran Consulting Group. https://www.corcoranccg.com/products/faqs/rpm-icare-home-tonometer-icare.

Li, Guorong, et al. "In vivo measurement of trabecular meshwork stiffness in a corticosteroid-induced ocular hypertensive mouse model." Proceedings of the National Academy of Sciences 116.5 (2019): 1714-1722.

Li, Guorong, et al. "Visualization of conventional outflow tissue responses to netarsudil in living mouse eyes." European journal of pharmacology 787 (2016): 20-31.

Li, Guorong, et al. "Trabodenoson, an adenosine mimetic with A1 receptor selectivity lowers intraocular pressure by increasing conventional outflow facility in mice." Investigative ophthalmology & visual science 59.1 (2018): 383-392.

Li, Guorong, et al. "Pilocarpine-induced dilation of Schlemm's canal and prevention of lumen collapse at elevated intraocular pressures in living mice visualized by OCT." Investigative ophthalmology & visual science 55.6 (2014): 3737-3746.

Mariakakis, Alexander, et al. "A smartphone-based system for assessing intraocular pressure." 2016 38th Annual International Conference of the IEEE Engineering in Medicine and Biology Society (EMBC). IEEE, 2016.

McDonnell, Fiona, et al. "Shear stress in Schlemm's canal as a sensor of intraocular pressure." Scientific reports 10.1 (2020): 5804.

McDonnell, Fiona, et al. "Pharmacological regulation of outflow resistance distal to Schlemm's canal." American Journal of Physiology-Cell Physiology 315.1 (2018): C44-C51.

Millard, L. H., D. F. Woodward, and W. D. Stamer. "Prostaglandin EP4 Receptor Activation Increases Outflow Facility in Perfused Human Eyes." Investigative Ophthalmology & Visual Science 51.13 (2010): 151-151.

Nakakura, S. et al. Intraocular pressure of supine patients using four portable tonometers. Optom. Vis. Sci. 90, 700-706 (2013).

(56) References Cited

OTHER PUBLICATIONS

Patel, Gaurang, et al. "Molecular taxonomy of human ocular outflow tissues defined by single-cell transcriptomics." Proceedings of the National Academy of Sciences 117.23 (2020): 12856-12867.
Pearce, J. G. & Maddess, T. The Clinical Interpretation of Changes in Intraocular Pressure Measurements Using Goldmann Applanation Tonometry: A Review. J. Glaucoma 28, 302-306 (2019).
Perkumas, K. M., and W. D. Stamer. "Protein markers and differentiation in culture for Schlemm's canal endothelial cells." Experimental eye research 96.1 (2012): 82-87.
Perkumas, K. M., et al. "Myocilin-associated exosomes in human ocular samples." Experimental eye research 84.1 (2007): 209-212.
Quigley, Harry A., and Aimee T. Broman. "The number of people with glaucoma worldwide in 2010 and 2020." British journal of ophthalmology 90.3 (2006): 262-267.
Ramos, Renata F., and W. Daniel Stamer. "Effects of cyclic intraocular pressure on conventional outflow facility." Investigative ophthalmology & visual science 49.1 (2008): 275-281.
Ramos, Renata F., et al. "Schlemm's canal endothelia, lymphatic, or blood vasculature?." Journal of glaucoma 16.4 (2007): 391-405.
Ren, Ruiyi, et al. "Netarsudil increases outflow facility in human eyes through multiple mechanisms." Investigative ophthalmology & visual science 57.14 (2016): 6197-6209.
Resnikoff, Serge, et al. "Estimated number of ophthalmologists worldwide (International Council of Ophthalmology update): will we meet the needs?." British Journal of Ophthalmology 104.4 (2020): 588-592.
Sherwood, Joseph M., et al. "Measurement of outflow facility using iPerfusion." PloS one 11.3 (2016): e0150694.
Smith, David W., and Bruce S. Gardiner. "Estimating outflow facility through pressure dependent pathways of the human eye." PloS one 12.12 (2017): e0188769.
Smith, David W., Chang-Joon Lee, and Bruce S. Gardiner. "Estimating outflow facility parameters for the human eye using hypotensive pressure-time data." Plos one 15.8 (2020): e0238146.
Spaide, Ted, et al. "Using deep learning to automate goldmann applanation tonometry readings." Ophthalmology 127.11 (2020): 1498-1506.
Stamer, W. D., et al. "Coiled-coil targeting of myocilin to intracellular membranes." Experimental eye research 83.6 (2006): 1386-1395.
Stamer, W. Daniel, et al. "Isolation, culture, and characterization of endothelial cells from Schlemm's canal." Investigative ophthalmology & visual science 39.10 (1998): 1804-1812.
Stamer, W. Daniel, et al. "eNOS, a pressure-dependent regulator of intraocular pressure." Investigative ophthalmology & visual science 52.13 (2011): 9438-9444.
Stamer, W. Daniel, et al. "Aquaporin-1 channels in human retinal pigment epithelium: role in transepithelial water movement." Investigative ophthalmology & visual science 44.6 (2003): 2803-2808.
Stamer, W. Daniel, et al. "Localization of aquaporin CHIP in the human eye: implications in the pathogenesis of glaucoma and other disorders of ocular fluid balance." Investigative ophthalmology & visual science 35.11 (1994): 3867-3872.
Sumida, Grant M., and W. Daniel Stamer. "S1P2 receptor regulation of sphingosine-1-phosphate effects on conventional outflow physiology." American Journal of Physiology-Cell Physiology 300.5 (2011): C1164-C1171.
Tonometer Market Size, Share And Trends Analysis Report By Type (Applanation, Rebound, Indentation, Dynamic Contour), By Portability (Desktop, Handheld), By End Use (Hospitals, Ophthalmic Centers), By Region, And Segment Forecasts, 2019-2026 (https://www.grandviewresearch.com/industry-analysis/tonometer-market#:~:text=The%20global%20tonometer%20market%20size,5.3%25%20over%20the%20forecast%20period.&text=Provision%20of%20favorable%20reimbursement%20policies,rate%20in%20hospitals%20and%20clinics.).
Tonometers. Ophthalmology 96, 196-198 (1989).
Tono-Pen-AVIA. https://www.reichert.com/products/tono-pen-avia.
Tonometer Market Size & Share Analysis—Growth Trends & Forecasts (2024-2029) Source: https://www.mordorintelligence.com/industry-reports/tonometer-market.
Toris, Carol B., and Carl B. Camras. "Measuring the outflow of aqueous humor." Glaucoma today 5.5 (2007): 15-22.
Wen, Joanne C., et al. "Intravitreal anti-VEGF injections reduce aqueous outflow facility in patients with neovascular age-related macular degeneration." Investigative ophthalmology & visual science 58.3 (2017): 1893-1898.
Wu, Yue, et al. "Development and validation of a machine learning, smartphone-based tonometer." British Journal of Ophthalmology 104.10 (2020): 1394-1398.
Yang, Jenny Number of eye care professional in the U.S. 2014-2020. (https://www.statista.com/statistics/448742/eye-care-professionals-in-the-us-forecast/).
Yool, Andrea J., W. Daniel Stamer, and John W. Regan. "Forskolin stimulation of water and cation permeability in aquaporin1 water channels." Science 273.5279 (1996): 1216-1218.

* cited by examiner

SYSTEMS AND METHODS FOR APPLANATION TONOMETRY AND TONOGRAPHY

CROSS REFERENCE TO RELATED APPLICATION

The present disclosure is a U.S. national counterpart application of PCT International Application No. PCT/2022/041931, filed Aug. 29, 2022, which claims priority to and the benefit of U.S. Provisional Patent Application No. 63/237,715, entitled "SYSTEMS AND METHODS FOR APPLANATION TONOMETRY AND TONOGRAPHY," filed on Aug. 27, 2021, the disclosure of each which is incorporated by reference herein in its entirety.

FIELD

The present disclosure relates to systems and methods for measuring intraocular pressure of the eye, and more particularly relates to the use of improved systems, devices, and methods for using tonography to make such measurements.

BACKGROUND

Tonometry is the measurement of intraocular pressure (IOP), which is the balance between the amount of fluid produced within the eye and the rate at which it exits the eye, termed "outflow facility." A method of measuring "outflow facility," in turn, can be referred to as tonography, where tonography is a procedure of recording tonometry measurement changes over a duration of time (e.g., IOP) with a device called a tonometer. IOP monitoring and treatment is key to diagnosing and managing eye conditions. More particularly, elevated IOP is the greatest risk factor for the development of glaucoma. Glaucoma is a progressive disease and accurate IOP measurements can be integral in its early detection and diagnosis. Once diagnosed, glaucoma management focuses on monitoring and lowering of IOP with medical and surgical interventions. Some clinical decisions are made based on very small changes in IOP. Thus, it is critical to be able to produce repeatable IOP measurements so that providers can have confidence in measured IOP changes.

The current clinical gold standard for measuring IOP is Goldmann applanation tonometry (GAT). While devices that use GAT have their benefits, there are also many drawbacks. This method relies strongly on human observation and is therefore prone to variability. GAT is subjective, prone to biased readings, and can have poor repeatability. Additionally, this method typically requires the use of expensive, bulky, often immobile equipment, which thus limits measurement of a patient's IOP to a clinical setting, and more particularly certain rooms where the equipment is already located. Other methods for measuring IOP exist, but they also have significant drawbacks. The existing limitations of other tonometers include high variability and poor agreement with GAT. For many methods, measurements require the application of topical anesthetic, therefore limiting measurements to the clinical setting. The use of anesthetics also necessarily requires additional steps and exposure to additional materials to perform the procedures. The various drawbacks of these systems result in a smaller number of measurements for a given patient than is desirable, which in turn limits physician insight into day-to-day IOP variation that could otherwise be relied upon to better inform the physician to provide a more targeted treatment.

Existing tonography methods also have significant drawbacks. For example, Schiøtz tonography and pneumatonography are poorly tolerated due at least due to long testing duration and suffering from poor repeatability. Fluorophotometry is another way to assess outflow facility. However, among other issues, obtaining a measurement using this technique can take several hours. There are also invasive techniques for measuring outflow facility, but any such techniques suffer from a number of problems, such as infection and risk of trauma to the eye due to need insertion. Further, ocular rigidity, pseudofacility, and uveoscleral outflow facility can confound the measurement.

Accordingly, there is a need for improved systems and methods to obtain objective intraocular pressure (IOP) measurements that are consistent, accurate, non-invasive, easy to use, and/or portable, as well as capable of generating tonographic measurements and/or outflow facility measurements.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

The present disclosure describes devices and methods used to measure intraocular pressure in the eye of a subject by using fixed force applanation tonometry. The present disclosure has benefits over current devices and systems because it is handheld, portable, and automated. The device applies a constant fixed force to the surface of the eye and an image capturing device obtains images of the area of the eye flattened under the force. A controller than uses an image-processing algorithm to automatically calculate the intraocular pressure from the resulting applanation images.

One exemplary embodiment of an applanation device includes a housing, an applanator, an image-capturing system, and a controller. The housing forms an internal cavity, and has an applanator access opening formed in an outer wall of the housing. The applanator access opening process access between the internal cavity and an outside environment. The applanator is disposed in the internal cavity of the housing. The applanator has a distal tip that is configured to pass into and through the applanator access opening to apply a force to an eye of a subject located in the outside environment. The distal tip can include one or more fiducial markings on it, for example to provide reference points for determining a reference distance upon which the controller can rely upon to calculate intraocular pressure.

The housing can provide for the applanation device to be a portable, handheld applanation device. In at least some embodiments, the device can include a power source disposed in the internal cavity of the housing. The power source can provide power to the image-capturing system and/or the controller. The image-capturing system can be disposed in the internal cavity of the housing and can be configured to capture a plurality of applanation images of the eye. The controller can also be configured to receive the plurality of applanation images captured by the image-capturing system and determine intraocular pressure in the eye based on the capture plurality of applanation images. The controller can be configured to be disposed inside the housing, or alternatively, it can be configured to be disposed outside of the housing. In the latter instance, the controller can be provided as part of a computer and/or a smartphone.

The force applied to the eye by the distal tip of the applanator can be a constant force for a duration of time during which the plurality of applanation images of the eye are captured. The distal tip can be conically-shaped and conformable. In at least some embodiments, the distal tip can be monolithic. The image-capturing system can include at least one camera. In some embodiments, the applanation device can also include at least one illumination source. The illumination source(s) can be disposed in the housing and can be configured to supply light to the distal tip.

The applanation device can include a lever arm and a counterweight. The lever arm can have a first end, a second end, and a fulcrum disposed between the two ends. The counterweight can be disposed on a second side of the fulcrum, more proximate to the second end than the first end, while the distal tip can be disposed on a first side of the fulcrum, more proximate to the first end than the second end. In at least some such embodiments, the applanation device can also include a constant force spring that can be coupled to the lever arm. The constant force spring can be configured such that the force applied to the eye by the distal tip of the applanator is a constant force.

The applanation device can include a sensor(s). The sensor(s) can be configured to measure the force applied by the distal tip to the eye and communicate the measured force to the controller. Alternatively, or additionally, the applanation device can include a force-adjustment mechanism, which in at least some embodiments, can be associated with the housing. The force-adjustment mechanism can be in communication with the applanator, and further, it can be configured to change an amount of the force being applied to the eye. The controller can be further configured to be in communication with the applanator such that the controller can direct a change in an amount of the force being applied to the eye.

The controller can be configured to identify an outer reference circle that is representative of a circumference of the distal tip and an inner circle that is representative of an applanation mire such that a surface area of the applanation mire can be determined. Accordingly, the intraocular pressure of the eye can be determined based on the determined surface area of the applanation mire and an amount of the force applied to the eye. In at least some embodiments the controller can be configured to remove from consideration one or more images of the plurality of applanation images captured by the image-capturing system to speed up processing time to determine intraocular pressure in the eye. This removal can be based on, for example: (a) one or more identified contours of the image(s); and/or one or more starburst ellipses approximated from the image(s). In at least some embodiments where such removal is based at least one the one or more identified contours of the image(s), parameters of the contours on which such removal can be based include at least one of: (a) a contour area; (b) a contour size; (c) a contour location; and/or (d) an eccentricity of the contour after fit to an ellipse.

The applanation device of any of the instances provided above, or elsewhere herein, can be configured to be used both when the subject is in a supine position and when the subject is in an upright position.

One exemplary method of measuring at least one of intraocular pressure in an eye or an outflow facility of an eye includes placing a distal tip of an applanator on a surface of an eye of a subject to cause a fixed force to be applied to the eye, capturing a plurality of applanation images of the eye while the fixed force is applied to the eye, and operating a processor to use information from the applanation images and the fixed force to determine at least one of intraocular pressure in the ye or an outflow facility of the eye.

In at least some embodiments, the applanator can include a lever arm and a counterweight. The lever arm can have a first end, a second end, and a fulcrum disposed between the two ends. The counterweight can be on a second side of the fulcrum, more proximate to the second end than the first end, while the distal tip can be disposed on a first side of the fulcrum, more proximate to the first end than the second end. The counterweight can supply a counter fixed force to enable application of the fixed force to the eye. The applanator can be disposed within a housing of a portable, handheld applanation device.

The method can include measuring a value of the fixed force and communication that measured value of the fixed force to the processor. The method can also include adjusting a value of the fixed force to a prescribed value. This can include, for example, causing the distal tip to apply the fixed force at a preset value such that the preset value becomes the adjusted value. This can also include, for example, operating one or more controls associated with the applanator to adjust the value of the fixed force across a plurality of values.

In some embodiments the method can include operating at least one of the processor or a separate processor to identify from the plurality of applanation images an outer reference circle that is representative of a circumference of the distal tip of the applanator and an inner circle that is representative of an applanation mire. This can be done to determine a surface area of the applanation mire, which can be information from the applanation images that is used to determine the intraocular pressure in the eye. In some such embodiments, the method can include using one or more fiducial markings on the distal tip of the applanator to provide reference points used in conjunction with the information from the applanation images to determine the intraocular pressure in the eye.

The method can include operating at least one of the processor or a separate processor to remove from consideration one or more images of the plurality of applanation images captured by the image-capturing system to speed up processing time to determine intraocular pressure in the eye. This can include removing the image(s) from consideration based on, for example: (a) one or more identified contours of the image(s); and/or one or more starburst ellipses approximated from the image(s). In at least some embodiments where such removal is based at least one the one or more identified contours of the image(s), parameters of the contours on which such removal can be based include at least one of: (a) a contour area; (b) a contour size; (c) a contour location; and/or (d) an eccentricity of the contour after fit to an ellipse.

In at least some embodiments, both intraocular pressure in the eye and the outflow facility of the eye are measured during the same procedure. In at least some embodiments, the subject is able to be in either a supine position or an upright position when placing the distal tip of the applanator on the surface of the eye of the subject and when capturing the plurality of applanation images of the eye while the fixed force is applied to the eye.

Any of the features or variations described herein can be applied to any particular aspect or embodiment of the present disclosure in a number of different combinations. The absence of explicit recitation of any particular combination is due solely to avoiding unnecessary length or repetition.

BRIEF DESCRIPTION OF THE DRAWINGS

This disclosure will be more fully understood from the following detailed description taken in conjunction with the accompanying drawings, in which.

DETAILED DESCRIPTION

Figure 1B:
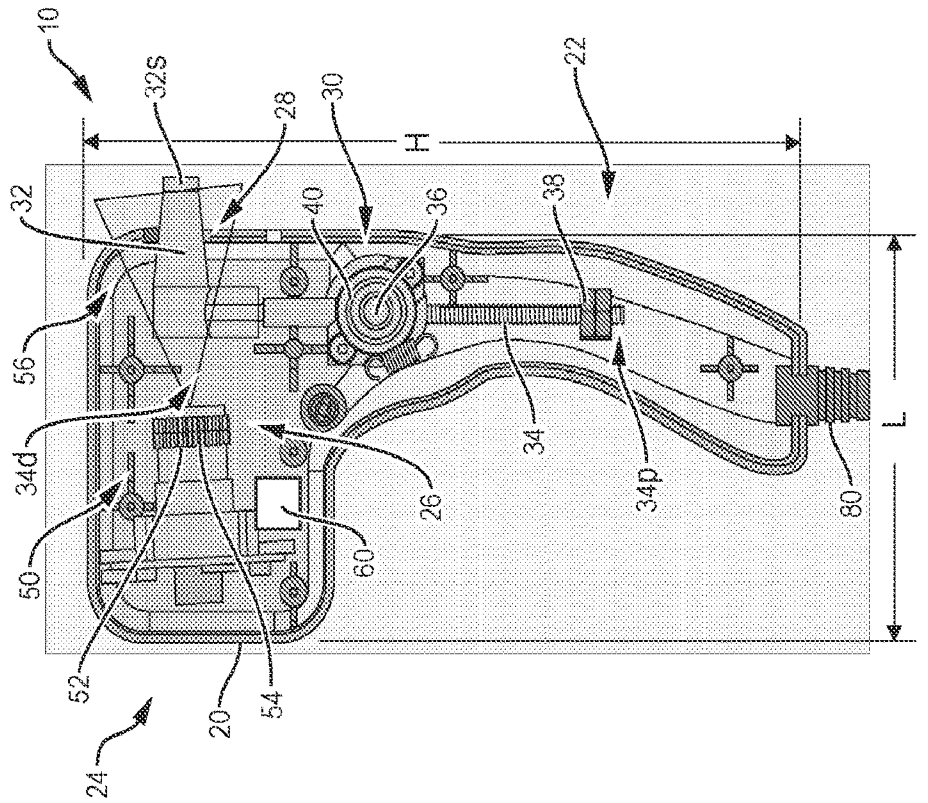
FIG. 1B is a side view of the applanation device of FIG. 1 having a portion of a housing removed such that internal components thereof are viewable.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Articles "a" and "an" are used herein to refer to one or to more than one (i.e., at least one) of the grammatical object of the article. By way of example, "an element" means at least one element and can include more than one element. "About" is used to provide flexibility to a numerical range endpoint by providing that a given value may be "slightly above" or "slightly below" the endpoint without affecting the desired result. The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations where interpreted in the alternative ("or").

Moreover, the present disclosure also contemplates that in some embodiments, any feature or combination of features set forth herein can be excluded or omitted. To illustrate, if the specification states that a complex comprises components A, B and C, it is specifically intended that any of A, B, or C, or a combination thereof, can be omitted and disclaimed singularly or in any combination. Similarly, to the extent features or actions are described herein as being a "first feature" or "first action," or a "second feature" or "second action," such numerical ordering is generally arbitrary, and thus such numbering can be interchangeable. Moreover, a person skilled in the art will appreciate that not all of the method steps or actions disclosed herein are required, and, in view of the present disclosure, will understand how modifications can be made to each step, the order of the steps, the limitation of certain steps, etc. without departing from the spirit of the present disclosure while still achieving the desired goals.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as approximately in the range of about 1% to about 50%, it is intended that values such as approximately in the range of about 2% to about 40%, approximately in the range of about 10% to about 30%, or approximately in the range of about 1% to about 3%, etc., are expressly enumerated in this specification. These are only examples of what is specifically intended, and all possible combinations of numerical values between and including the lowest value and the highest value enumerated are to be considered to be expressly stated in this disclosure, as are values slightly above and/or slightly below those ranges at least in instances in which the term "about" is used. A number of terms may be used throughout the disclosure interchangeably but will be understood by a person skilled in the art. By way of non-limiting example, the terms "constant" and "fixed" may be used interchangeably when referring to the force applied to the surface of the eye.

Unless otherwise defined, all technical terms used herein have the same meaning as commonly understood by one of ordinary skill in the art to which this disclosure belongs. Additionally, like-numbered components across embodiments generally have similar features unless otherwise stated or a person skilled in the art would appreciate differences based on the present disclosure and his/her knowledge. Accordingly, aspects and features of every embodiment may not be described with respect to each embodiment, but those aspects and features are applicable to the various embodiments unless statements or understandings are to the contrary.

The present disclosure provides for applanation devices, and associated methods, for performing tonometry, and in turn methods of performing tonography, which is for measuring an outflow facility associated with the eye (i.e., the rate at which fluid produced by the eye exists the eye). The devices and methods disclosed provide portable devices for the convenient and easy determination of intraocular pressure (IOP) in an eye. A constant force is applied by a distal tip of an applanator to an eye, enabled by a counterweight disposed on an opposite side of the applanator, and then an imaging capture system is able to record a plurality of images while the constant force is being applied to the eye. A control system, which can be part of the applanation device or in communication with the same (e.g., by way of a smartphone or other computing device, which can run an associated application or "app"), an then operate using an algorithm disclosed herein for determining IOP based at least on information recorded in the captured images and the value of the constant force applied to the eye. The applanation device can be a portable, handheld device, operable by a clinician or physician. It is contemplated that the disclosures provided for herein can also enable embodiments that can be used at home by patients, i.e., outside of a clinical setting.

Figure 1A:
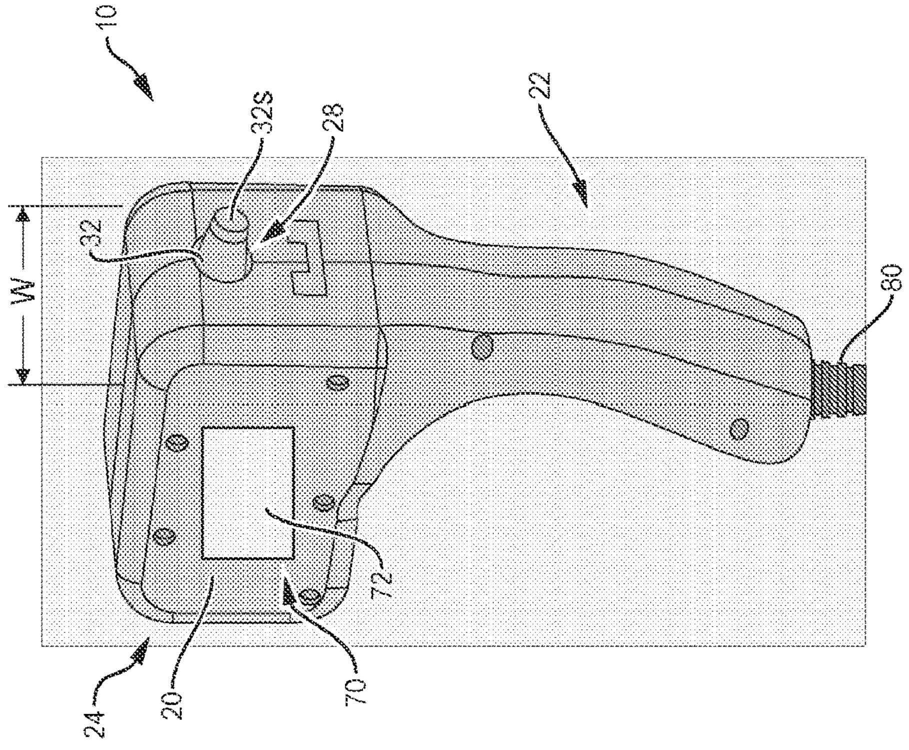
FIG. 1A is a perspective view of one exemplary embodiment of an applanation device.

FIGS. 1A and 1B illustrate a non-limiting exemplary embodiment of an applanation device 10 capable of measuring IOP in the eye of a subject. As shown, the device 10 can be defined by a handheld housing 20, and can include an applanator 30, an image-capturing system 50, and, at least in some embodiments, a controller 60. In some other embodiments, the controller 60 can be provided by an outside device, such as a computer or smartphone, which may or may not be considered part of the applanation device 10.

In the illustrated embodiment, the housing 20 includes a handle portion 22, which can be a location where a user can wrap his or hand around to operate the device 10, and a component portion 24, which can be a location where the various operating components of the device 10 can be disposed. More particularly, as shown in FIG. 1B, the component portion 24 has an internal cavity 26 formed therein for housing the operating components of the device 10, among other components of the device 10. FIG. 1B illustrates the applanation device 10 with a portion of the housing 20 removed for viewing of the components disposed therein. In at least some embodiments, the housing 20 can be configured to be separated into two or more components to allow access to the internal cavity 26 and components disposed therein. This can be achieved, for example, by one or more mechanical mechanisms known to those skilled in the art for mechanically coupling two components together, including but not limited to a snap fit, one or more male-female connectors, threaded connections, magnetic coupling, etc.

The housing 20, and thus the handle portion 22 and the component portion 24, can have a variety of shapes, features, and sizes, with designs of the handle portion generally being conducive for easy gripping by a user, and designs of the component portion 24 generally being conducive to house components that enable the device to perform its intended function, i.e., measuring IOP using the techniques and features described herein. For example, the housing 20 can be sized to be portable and handheld, with the handle portion 22 shaped and sized to fit a human hand and the component portion shaped and sized to be a rectangular prism.

The operable components of the applanation device 10 (e.g., the applanator 30, the image-capturing system 50, and, at least in some embodiments, the controller 60) can be disposed, at least partially, in the internal cavity 26. The phrase "at least partially" is appropriate, as described in greater detail below, at least because at least some portion of one or more components (e.g., a distal tip 32 of the applanator 30) can be configured to pass out of the internal cavity 26 and the housing 20 at least during use. More particularly, the housing 20 can include an applanator access opening 28 formed in an outer wall of the housing 20. The applanator access opening 28 provides access between the internal cavity 26 and an outside environment such that a portion of the applanator 30 can pass therethrough to access the outside environment, such as to contact a subject's eye. The "at least partially" phrase may also be applicable to aspects of the image-capturing system 50 and/or the controller 60 as well.

Figure 2B:
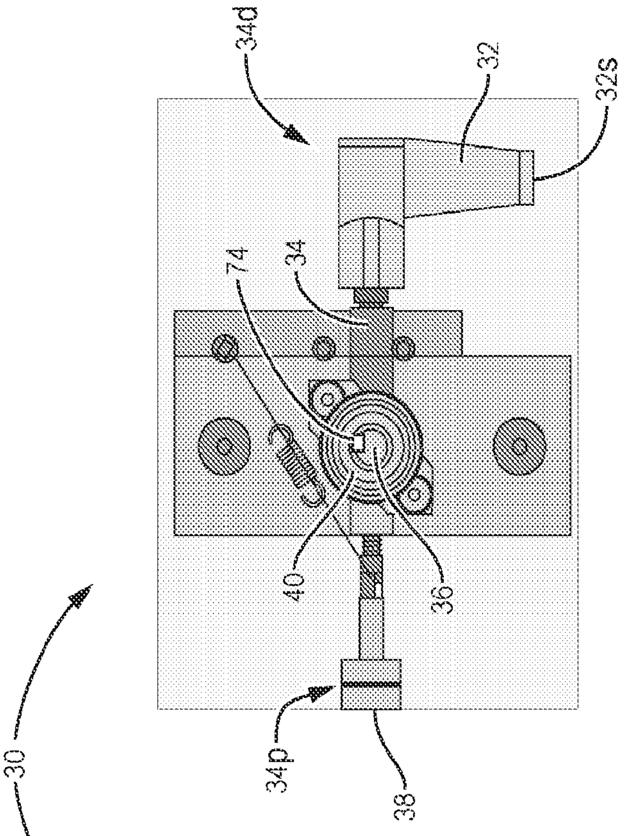
FIG. 2B is the side view of the applanator of FIG. 2A in a second orientation.
Figure 2A:
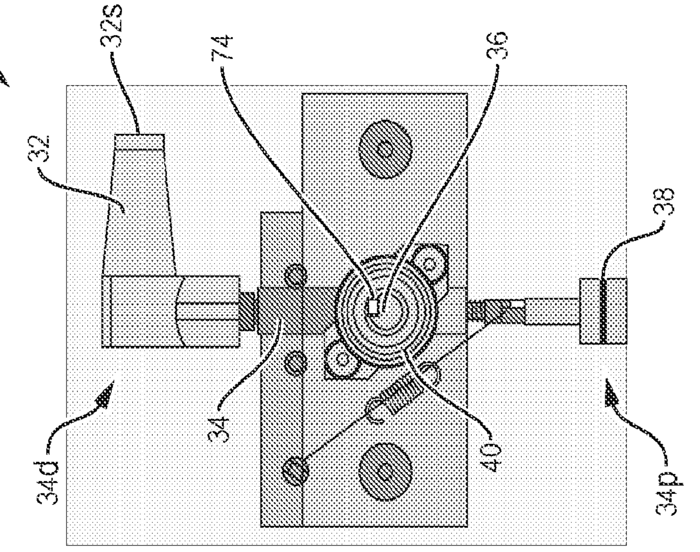
FIG. 2A is a side view of an applanator of the applanation device of FIG. 1A, the applanator being in a first orientation.

The applanator 30 of the applanation device 10, sometimes referred to as a force-applying mechanism or force applier 30, is illustrated in greater detail in FIGS. 1B, 2A, and 2B. As shown, the applanator can include a lever arm 34 having proximal and distal ends 34*p*, 34*d*, also referred to as first and second ends 34*p*, 34*d*, and a fulcrum 36 disposed therebetween. A constant force mechanism 40 can be coupled to or otherwise associated with the lever arm 34, such as by being disposed proximate to or at the fulcrum 36. The distal tip 32 can be disposed on a first side of the fulcrum 36 (i.e., more proximate to the distal end 34*d* than the proximal end 34*p*), for example as shown at the distal end 34*d*, while one or more counterweights 38 can be disposed on a second side of the fulcrum 36 (i.e., more proximate to the proximal end 34*p* than the distal end 34*d*), for example as shown at the proximal end 34*p*.

Figure 5:
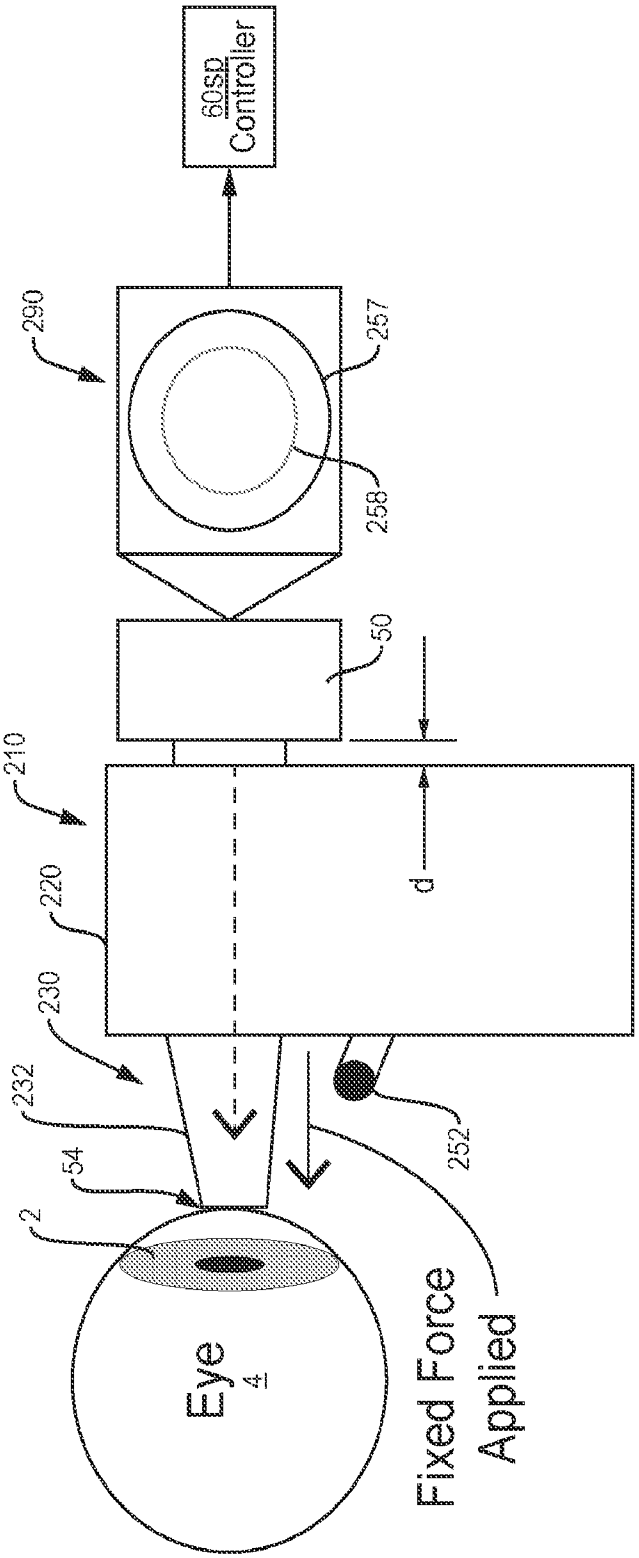
FIG. 5 is a schematic illustration of one embodiment of an applanation device in use.

The distal tip 32 can include a terminal end surface 32*s* configured to contact a cornea at a surface of an eye of a subject (see FIG. 5). The distal tip 32 can apply a constant force, also referred to as a fixed force, to flatten the contacted cornea to a fixed area. As described in greater detail below, the image-capturing system 50 can be operated to capture images during the time the constant force is being supplied by the applanator 30, and more specifically the distal tip 32. The distal tip 32 can have a variety of shapes and sizes, including but not limited to a conventional or customized prism. In the non-limiting illustrated embodiment, the distal tip 32 is conically-shaped (e.g., it is cone-shaped), and thus the terminal end surface 32 is a flat, substantially circular surface. A person skilled in the art will appreciate other shapes and configurations that can be used for the distal tip 32. The distal tip 32 can be made from a conformable material, such as acrylic, polycarbonate, polyether ether ketone (PEEK), silicone, urethane, polyurethane, and/or other transparent polymers, among other materials. The material can often be translucent. Optionally, the distal tip 32 can be coated with a compliant material, such as a hydrogel, that can provide benefits that include allowing the distal tip 32 to contact the cornea without the need for anesthesia. In some embodiments, the distal tip 32 can be a monolithic part with no splits or slits formed therein.

Figure 3B:
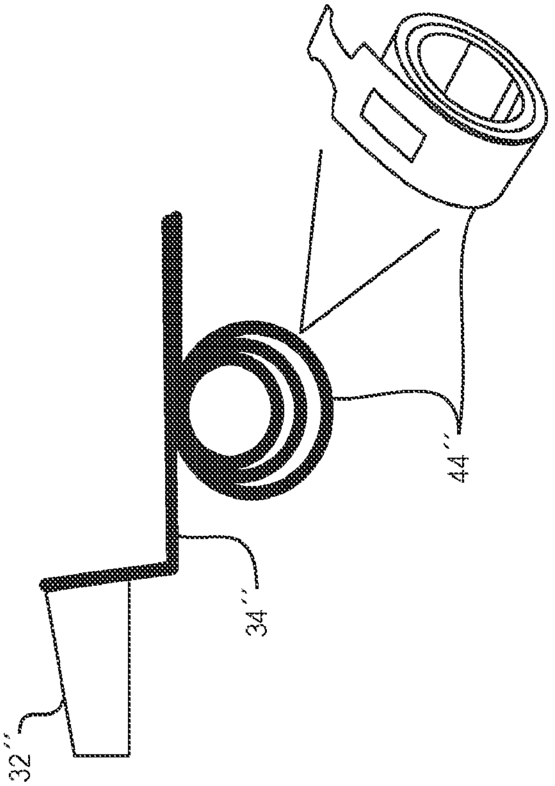
FIG. 3B is a side schematic view of still another embodiment of an applanator that can be used as part of an applanation device.
Figure 3A:
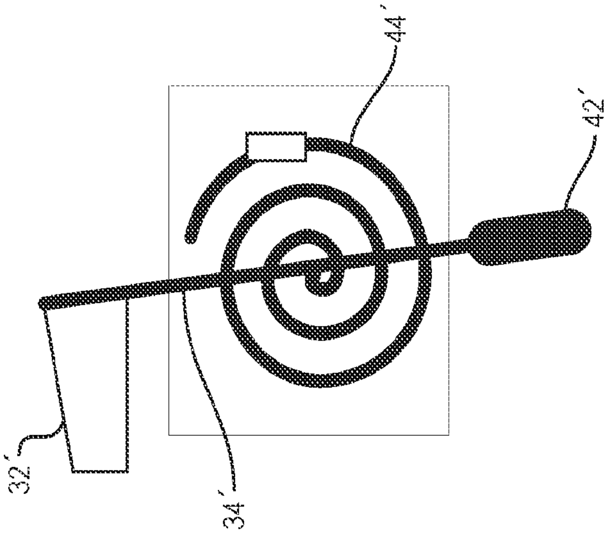
FIG. 3A is a side schematic view of another embodiment of an applanator that can be used as part of an applanation device.

The application of a constant force by the distal tip 32 can be enabled by the constant force mechanism 40 associated with the lever arm 34. In the illustrated embodiment the constant force mechanism 40 is disposed at the fulcrum 36, although a person skilled in the art will appreciate other configurations are possible such that the constant force mechanism 40 can be disposed at other locations along the lever arm 34. The constant force mechanism 40 can be any of a variety of mechanical components known by those skilled in the art for supplying a constant force, including but not limited to various springs. FIGS. 3A and 3B illustrate two such springs 40',40" that can serve as constant force mechanisms.

As shown in FIG. 3A, the spring 40' is a torsional spring, thus forming a torsional spring constant force mechanism, configured to apply a constant force to a lever arm 34', and in turn a distal tip 32' of the lever arm 34'. The lever arm 34' can include one or more counterweights 38' disposed on an opposite side of the lever arm 34' with respect to the distal tip 32', which as described below, can help maintain the location of the distal tip 32' to supply the constant force supplied by the spring 40'. Similarly, as shown in FIG. 3B, the spring 40" is a linear spring, thus forming a linear spring constant force mechanism, configured to apply a constant force to a lever arm 34", and in turn a distal tip 32" of the lever arm 34". The lever arm 34" can include one or more counterweights 38" disposed on an opposite side of the lever arm 34" with respect to the distal tip 32", which as described below, can help maintain the location of the distal tip 32" to supply the constant force supplied by the spring 40".

In other embodiments, the constant force can be generated through a variety of mechanisms and means known to those skilled in the art conducive for such use in view of the present disclosures, including but not limited to a torsional spring force (including but not limited to the embodiment illustrated in FIG. 3A), a linear spring force (including but not limited to the embodiment illustrated in FIG. 3B), a gravitational force, a counterbalance force, and/or magnetic force. For example, gravitational force can be used to generate constant force in subjects laid in a supine position. The other forces described herein may be more suitable for subjects in an upright position. The foregoing notwithstanding, a person skilled in the art, in view of the present disclosures, will appreciate any the methods, devices, and systems, provided for herein can be adapted for use in either or both the upright or supine positions.

Turning back to the configuration of FIGS. 1B, 2A, and 2B, the constant force applied to the cornea by the distal tip 32 can also be the result, at least in part, of the counterweight(s) 38 disposed on an opposite side of the fulcrum 36 from the distal tip 32. The counterweight(s) 38 supply a counter fixed force to enable application of the constant force to the object outside of the applanation device 10, e.g., the cornea of the eye, by the distal tip 32 of the applanator 30. In other words, the force applied at the distal tip 32 can be limited to the magnitude of the counteracting force provided by the counterweight(s) 38, or a ratio thereof. The amount of weight of the counterweight(s) 38, in conjunction with a location of the counterweight(s) 38 along the lever arm 34 impacts an amount of force the distal tip 32 provides to an object with which it is in contact (e.g., a cornea) and/or the ability of the distal tip 32 to maintain the application of the force to the outside object. As the amount of weight of the counterweight(s) 38 increases and/or a distance from the fulcrum 36 the counterweight(s) 38 are disposed increases, the amount of force supplied by the distal tip 32 to an object with which it is in contact can also increase and/or the amount of force that can be constantly supplied by the distal tip 32 can increase. The steady location and amount of weight, and thus force, supplied by the counterweight(s) 38 allows the force supplied by distal tip 32 to be constant by allowing the distal tip 32 to be held in place. A person skilled in the art will appreciate that the configuration of the applanator 30, including but not limited to the distal tip 32, the lever arm 34, the counterweight(s) 38, and/or the constant force mechanism 40, can be altered as described above or otherwise understood by a person skilled in the art such that adjustment of a counterweight(s) does not provide a ratio of 1:1 change to the amount of force supplied by the distal tip 32, and that configurations can be provided that are not a 1:1 ratio adjustment between the counterweight(s) 38 and the distal tip 32. The ratio can be on either end of the spectrum, meaning a change of counterforce supplied by the counterweight(s) 38 can be larger than a change of force supplied by the distal tip 32, or a change of counterforce supplied by the counterweight(s) 38 can be smaller than a change of force supplied by the distal tip 32.

As shown, two counterweights 38 are disposed at the proximal end 34*p* of the lever arm 34, though a person skilled in the art will appreciate fewer or more counterweights can be used and can be disposed at other locations along the lever arm 34, typically more proximate to the proximal end 34*p* than the distal end 34*d* of the lever arm 34. Different sized and shaped counterweights 38 can be provided. In at least some embodiments, mechanical mechanism can be provided that enable the effect of the counterweights 38 to be adjusted by a user. This can include selectively including or not including a counterweight on the lever arm to provide a force that in turn causes the distal tip 32 to provide a force on the cornea (or other object in the outside environment on which the distal tip 32 contacts) and/or selectively sliding one or more of the counterweights 38 along the lever arm 34. A person skilled in the art, in view of the present disclosures, will understand how the counterweight(s) 38 can be maneuvered with respect to the lever arm 34 to change an amount of force that is in turn supplied by the distal tip 32 and/or able to be maintained by the distal tip 32.

FIGS. 2A and 2B illustrate operation of the applanator 30. In the configuration of FIG. 2A, the applanator 30 is in a substantially vertical configuration such that the constant force mechanism 40 is not applying a constant force to the distal tip 32. When viewed in the context of the applanation device 10 as a whole, the entirety of the applanator 30 can be disposed within the housing 20 and/or at least the distal tip 32 is not providing a constant force to an object if even in this configuration the distal tip 32 passes through the opening 28. A person skilled in the art will appreciate that although this configuration is described as a substantially vertical configuration, the applanator 30 may or may not be disposed substantially vertically with respect to a ground plane (i.e., a plane defined by a ground on which a subject and/or operator of the applanation device may be standing, seated with respect to, etc.). The applanator 30 may be disposed at an angle with respect to the ground plane while in this configuration without departing from the spirit of the present disclosure. More generally the configuration of FIG. 2A is intended to illustrate the applanation device 10 in unengaged configuration in which a constant force is not being applied to an object, such as a cornea of a subject's eye.

FIG. 2B illustrates the applanator 30 in a substantially horizontal configuration such that the constant force mechanism 40 is applying a constant force to the distal tip 32. A person skilled in the art will appreciate that this illustrated configuration is an exaggeration of how the applanator 30 would move within the confines of the applanation device 10. This is at least because in this illustrated embodiment there is no housing 20 to help constrain movement of the applanator 30. This figure nevertheless properly illustrates how a constant force can be supplied by the constant force mechanism 40, in turn causing the distal tip 32 to rotate, as shown in a clockwise direction with respect to the fulcrum 36. In the context of the embodiment of FIGS. 1A and 1B, this causes the distal tip 32 to exit the internal cavity 26, pass through the applanator access opening 28, and into an outside environment, where it can supply a constant force to an object, such as a cornea of a subject's eye. While the distal tip 32 can be enabled to move freely within and out of the applanator access opening 28, the constant force supplied to the distal tip 32 as described herein can limit such free movement In at least some embodiments, the applanation device 10 can include a force-adjustment mechanism 70, which can be in communication with the applanator 30 and configured to change the amount of force applied to the surface of the eye. The force-adjustment mechanism 70 can include an input interface 72 such as a touch screen (as shown), dial, and/or buttons coupled with and/or disposed on the housing 20 and configured to receive an input of desired magnitude of force from the user. The force-adjustment mechanism 70 can then communicate the desired amount of force to the applanator 30 by a variety of means including mechanically and/or electrically. In a non-limiting exemplary embodiment, the user enters the desired force in the input interface 72 and the force-adjustment mechanism 70 can directly engage with the applanator 30 to apply the desired force to the surface of the eye, via the distal tip 32. By way of example, when the force-adjustment mechanism 70 includes a constant force mechanism 40 like a torsional spring or torsional spring mechanism, adjusting the torsion on the spring can induce a different force to be applied. Adjustment of the force can be achieved, for instance, by adjusting the position, mass, and/or weight of the counterweight(s) 38 and/or adjusting the position and/or location of the constant force mechanism 40, a different force can be supplied. In some embodiments, the controller 60 can act as the force-adjustment mechanism, or as part of the force-adjustment mechanism, such as by providing such communication to alter a force being supplied by the applanator 30, as further described below.

Further, the magnitude of the constant force supplied by the applanator 30 can be tuned to a prescribed level by way of the force-adjustment mechanism 70. In some embodiments, the force-adjustment mechanism 70 can include one or more preset values (e.g., values of force) that can be accessed by a user and/or be programmed by a user. It may be desirable, for example, to have different force levels for patients experiencing extreme eye pressure, such as advanced glaucoma or after glaucoma surgery. In a non-limiting example, the constant force can be set approximately in the range of about two (2) grams to about fifteen (15) grams. As provided for herein, a magnitude or value of the constant force supplied by the applanator 30 can be tuned, for example by adjusting the value to a prescribed value. As the force is adjusted, one or more prescribed values can become the adjusted value, i.e., the value to which the applanator 30 is adjusted to apply. This can also include, for example, operating one or more controls associated with the applanator 30 to adjust the value of the fixed force across a plurality of values. In some embodiments, one or more sensors 74 (see FIGS. 2A and 2B) can be provided that can measure the force applied by the distal tip 32 to the eye of the subject and communicates the measured force to the controller 60, the force-adjustment mechanism 70, and/or other components associated with the same (e.g., an app). In the illustrated embodiment, the sensor 74 is disposed on the constant force mechanism 40, although in other embodiments it can be disposed on the distal tip 32, the counterweight(s) 38, and/or other components of the applanator 30 or applanation device 10 that are able to detect an amount of force being supplied to an object in the outside environment (e.g., the cornea of a subject) by the distal tip 32. In response to the values of force detected by the sensor(s) 74, a user can make an adjustment to the amount of force being supplied by the applanator 30 and/or a controller and/or related components (e.g., an app) can make automatic adjustments to an amount of force being supplied by the applanator 30.

The applanation device 10 also includes the image-capturing system 50. A person skilled in the art, in view of the present disclosures, will understand suitable components of such a system that can be incorporated into the applanation device 10. In some embodiments, such as the one illustrated with respect to FIGS. 1B, 2A, and 2B, the image-capturing system 50 comprises a camera 52. The camera 52 can be sized to fit within the housing 20 and can be configured to capture a plurality of images during the time the distal tip 32 is supplying a force to an outside object (e.g., a cornea of a subject). The camera 52 can be positioned so that the distal tip 32 is always in the field of view of the camera 52 as it swings from its initial position (e.g., located within and/or proximate to the applanator access opening 28) to its final position (e.g., a position furthest from an initial position along a path of travel for the distal tip 32 and/or a position where the distal tip 32 is intended to contact a subject's eye). In at least some embodiments, an illumination source or light source 54 can be provided that can provide light to the distal tip 32, and thus to an object in the outside environment engaged by the same (e.g., a cornea of a subject). In the illustrated embodiment the light source 54 is part of the camera 52, providing light by an illustrated cone of light 56, but in other embodiments the light source can be separately disposed in the housing 20 and/or can be provided from outside of the housing 20 of the applanation device 10. For example, the illumination source 54 can be disposed externally on a surface of the housing 20, proximal to the applanation access opening 28. The illumination source 54 can be electrically connected with a switch to power the source on and off. In some embodiments, the image-capturing system 50 can be designed to be triggered to begin recording a video, capturing images, and/or otherwise providing audio and/or visual feedback. For example, in instance when an algorithm (described in greater detail below) is run in real-time in conjunction with using the applanation device 10, when a stable measurement is detected, it can trigger the video recording, image capturing, and/or otherwise providing audio and/or visual feedback. Further, while the image-capturing system 50 is sized to fit within the housing 20, in other embodiments at least a portion of the image-capturing system 50, or an entire image-capturing system, can be disposed outside of the housing 20, while still having the ability to capture images during the time the distal tip 32 is supplying a force to an outside object (e.g., a cornea of the subject). The system can include, for example, a camera associated with a smartphone.

A controller 60 can also be included as part of the applanation device 10. This can include having the controller 60 disposed within the housing 20 and/or can involve communicating with the applanation device 10. Alternatively, the controller 60 may be considered a separate component that is not part of the applanation device 10. The controller can operate aspects of the algorithm described below with respect to FIG. 5 and is further described below with respect to FIG. 6. Similar to the image-capturing system 50, the controller 60 can be part of a smartphone, including but not limited to the same smartphone that is used as part of the image-capturing system and/or that runs an algorithm as provided for below.

As shown, the applanation device 10, including components thereof (e.g., the camera 52, the light source 54, the controller 60, portions of the force adjustment mechanism 70, etc.), can be powered by one or more power sources. In the illustrated embodiment, a connected cord or wire, such as a power cord 80, can be provided to deliver power from an outside source, such as AC or DC power source, to the applanation device 10. In other embodiments, one or more batteries (rechargeable or other acceptable battery type for use in such a device) can be provided in the internal cavity 26 of the housing 20 to provide desired power to the various components of the applanation device 10.

Figure 4B:
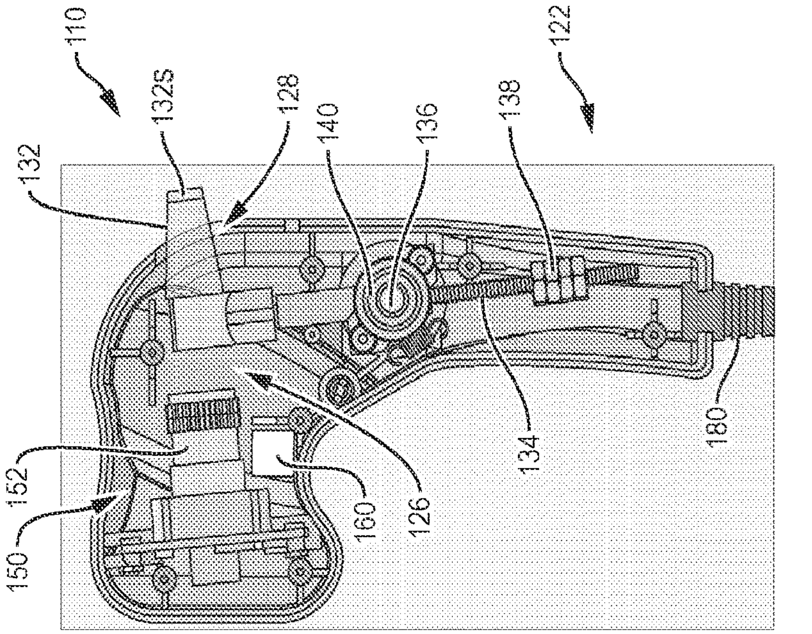
FIG. 4B is a side view of the applanation device of FIG. 3A having a portion of a housing removed such that internal components thereof are viewable.
Figure 4A:
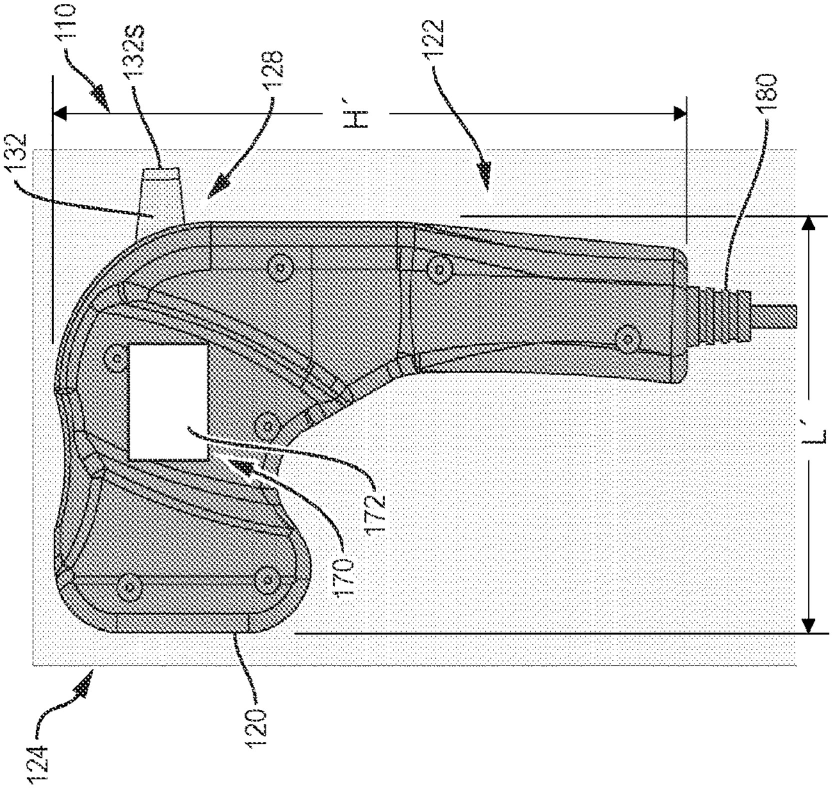
FIG. 4A is a side view of another exemplary embodiment of an applanation device.

FIGS. 4A and 4B illustrate another non-limiting exemplary embodiment of an applanation device 110 capable of measuring IOP in the eye of a subject. The components of the device 110 are similar to those of the device 10, and thus repetitive explanations of the same are not necessary. A primary distinction between the device 110 and the device 10 is a shape of the handheld housing 120. More particularly, a component portion 124 of the handheld housing 120 is more curved than the component portion 24 of the applanation device 10. A handheld portion 122 of the housing 120 is not as ergonomically configured as the handheld portion 22 of the housing 20, but nonetheless achieves similar purposes. The other components of the device, including but not limited to those components that can be at least be partially disposed in an internal cavity 126 of the housing, such as an applanator 130, an image-capturing system 150, and, at least in some embodiments, a controller 160, can be similar to the akin components described above with respect to the applanation device 10. This is also true of the components thereof, including but not limited to an applanator access opening 128, a distal tip 132, a lever arm 134, a fulcrum 136, one or more counterweights 138, a constant force mechanism 140, a camera 152, an illumination or light source 154, a force-adjustment mechanism 170, an input interface 172, one or more sensors 174, and/or a power cord 180.

While the applanation devices of the present disclosures, e.g., the devices 10, 110, can have a variety of shapes, sizes, and configurations, impacted, at least in part, by the shape, size, and/or configuration of the components, the age, size, and anatomy of the subject, and/or the preferences of the user with respect to the way and type of measurements are being made, a general beneficial feature of the present disclosure is the portability of the applanation devices resulting from the present disclosures. Accordingly, as shown in FIGS. 1A, 1B, and 4A, a length L, L' of the housing 10, 110 can be approximately in the range of about 5 centimeters to about 15 centimeters, a height H, H' of the housing 10, 110 can be approximately in the range of about 10 centimeters to about 25 centimeters, and a width W, W' (the width W' is not visible in FIGS. 4A and 4B, but is representative of the same dimension illustrated in FIG. 1A) of the housing 10, 110 can be approximately in the range of about 2.5 centimeters to about 12 centimeters, and thus a length, height, and width of the applanation devices 10, 110 can be similar, accounting for changes in these dimensions that may occur due to some portion of its components (e.g., the distal tips 32, 132) extending outside of the housing 20, 120 in some configurations. In one non-limiting embodiment, a length of the housing is about 7.5 centimeters, a height of the housing is about 14 centimeters, and a width of the housing is about 5 centimeters, with variations of these dimensions while still being portable and handheld are possible. By way of comparison, a Goldmann tonometer, which is an attachment and not a handheld device that can be used on its own, has a length of about 8.5 centimeters, a height of about 17 centimeters, and a width of about 3.5 centimeters. The Goldmann tonometer, however, must be used in conjunction with a slit lamp ophthalmoscope, which itself would not be considered a portable, handheld device by a person skilled in the art. By way of further comparison, a Perkins tonometer has a length of about 4.5 centimeters, a height of about 23.5 centimeters, and a width of about 3 centimeters.

FIG. 5 is a schematic illustration of one embodiment of an applanation device 210 in use. As shown, the applanation device 210 is schematically illustrated without much detail. Unless otherwise noted, the applanation device 210 can include similar components, features, and capabilities as the other applanation devices provided for herein, e.g., the devices 10 and 110, or otherwise derivable from the present disclosures and thus further explanations of the components thereof is unnecessary. Accordingly, only a few components of the device 210 are described and illustrated with respect to FIG. 5. One difference in this illustrated embodiment is that an image-capturing system 250 is disposed outside of a housing 210 of the applanation device 210. The image-capturing system 250 is also schematically illustrated without much detail, but like the device 210, it can include similar components, features, and capabilities as the other image-capturing systems provided for herein, e.g., the systems 50 and 150, otherwise derivable from the present disclosures, and/or other image-capturing systems known to those skilled in the art. In the illustrated embodiment, the image-capturing system 250 is a camera or comparable device that is optimized for capturing high-resolution images at a prescribed distance d. A preferred value for the prescribed distance can be as close as possible while still allowing the distal tip 32 to be in the field of view of the camera 52 as it swings between its initial and final positions. As working distance increases, the applanation seen through the distal tip 32 takes up less of the field of view of the camera 52, in turn lowering the resolution of the applanation that may potentially impact the accuracy of the algorithm. In one non-limiting embodiment, a focusing range of the camera 52 is about 20 mm+ and the distance d between the lens of the camera 52 and the distal tip 32 is about 40 mm. In at least some embodiments, the image-capturing system 250 may be integrated into a computing device such as a smartphone, tablet, laptop, personal computer device, computer, or other similar computing device, such as by coupling to such a handheld device and using features of the handheld device to operate and/or communicate with the image-capturing system 250. In other instances, the image-capturing system 250 can be a camera provided as part of such a smartphone, tablet, laptop, personal computer device, computer, or other similar computing device. In still other instances, the image-capturing system 250 can be its own image-capturing device that is able to communicate capture images to such a smartphone, tablet, laptop, personal computer device, computer, or other similar computing device for use in conjunction with a controller, app, etc. as provided for herein.

The image-capturing system 250 can be substantially aligned with a distal tip 232 of an applanator 230 of the device 210 as shown in FIG. 5 and can be configured to capture a plurality of images 290 associated with a cornea 2 of an eye 4. The image 290 can capture an applanation surface or mire 258, and, it can also designate a reference surface 257, representative of a circumference of the distal tip 232 for example. In the embodiment, the image-capturing system 250 communicates the plurality of images to the controller 260, which in the illustrated embodiment is separately disposed from the housing 220 of the device 210, though other configurations are possible. The controller 260 can process these images 290, automatically and/or as directed by a user, by an algorithm 270 designed to find the area of the applanation surface, and therefore the intraocular pressure, as further described below.

In use, the distal tip 232 of the applanation device 210 extends from the housing 220, is placed on the surface of the eye 4, and it applies a constant, fixed force to the eye 4 to flatten the cornea 2 to define a fixed area. As a result of the present disclosures, the distal tip 232 can be applied to the eye of a subject in the upright or supine positions, and thus the device 210 itself can be used when a subject is in either such position. This is at least because the counterweight(s) and the constant force mechanism can be calibrated so that in a supine position, the device 210 provides a constant force, and then in an upright position, the weight of the counterweights can combine with the force of gravity, thus still allowing the device 210 to provide a constant force.

An illumination source 252, which in this instance is disposed outside of the housing 210, though as provided for elsewhere, it can be disposed in the housing, directs light to the distal tip 232 and onto the eye 4. The image-capturing system 250, substantially aligned with the distal tip 232 of the applanator 230, can capture a plurality of images of the applanation surface 258 while the constant force is applied. In some embodiments the image-capturing device 250 can record a video from which frames can be selected as the images 290. In some embodiments, a fluorescent yellow dye can be applied to the eye 4 prior to the application of the constant force by the distal tip 232. In the exemplary embodiment shown, the illumination source 252 can pass blue LED light towards and/or into the distal tip 232 and onto the dyed applanation surface of the eye 4. The blue hue can combine with the yellow dye to highlight the applanation surface 258 in a green outline, which can be present on the generated images 290. As shown in FIG. 5, the resulting image shows an outer circle or reference circle 257, which represents the area of the flat distal surface of the distal tip 232, and an inner circle 258, which represents the applanation surface or mire, which is the flattened area of contact between the distal tip 232 and cornea 4. The resulting applanation images can be communicated from the image-detecting device 250 to the controller 260 for further image processing. In at least some instances, the distal tip 232 can include one or more fiducial markings formed on a surface thereof to provide reference points for determining a reference distance upon which the controller can reply upon to calculate the IOP. More particularly, because the diameter of the distal tip 232 is known, the distal tip 232 can be identified and measured in the resulting image 290 and can be used to calculate a conversion factor from diameter in pixels to diameter in millimeters. This conversion can then be used to convert the applanation diameter from pixels to millimeters, and because the constant force being applied is known, the IOP can be calculated. In alternative embodiments, a person skilled in the art, in view of the one or more markings on the distal tip 232 of a known size and/or distance can be substituted as the reference for determining an applanation area.

The controller 260, as well as other controllers provided for herein, such as the controllers 60, 160, can be operable to receive the plurality of images from the image-capturing device 250, and further, can be configured to operate an image-processing algorithm 270 to process the image data and calculate the IOP of the eye 4. The controller 260 can contain a single processor or a plurality of processors to carry out the methods disclosed herein. As mentioned above, in some embodiments, the controller 260 can act in conjunction with or as part of a force-adjustment mechanism to direct a change in the force applied to the eye 4 by communicating with the applanator 230 of the applanation device 210, such as by mechanical and/or electrical means. For example, it can communicate by sending signals to the applanation device 210 to direct a change in the force applied by the distal tip 232 automatically and/or to an operate to make manual adjustments to the force applied by the distal tip 232. Alternatively, the controller 260 can work in conjunction with a separate force-adjustment mechanism to direct the change in force. The controller 260 can be a computing device such as a smartphone, tablet, laptop, personal computer device, computer, or other similar computing device. An exemplary embodiment of a controller 260 is described below with respect to FIG. 7.

Figure 6:
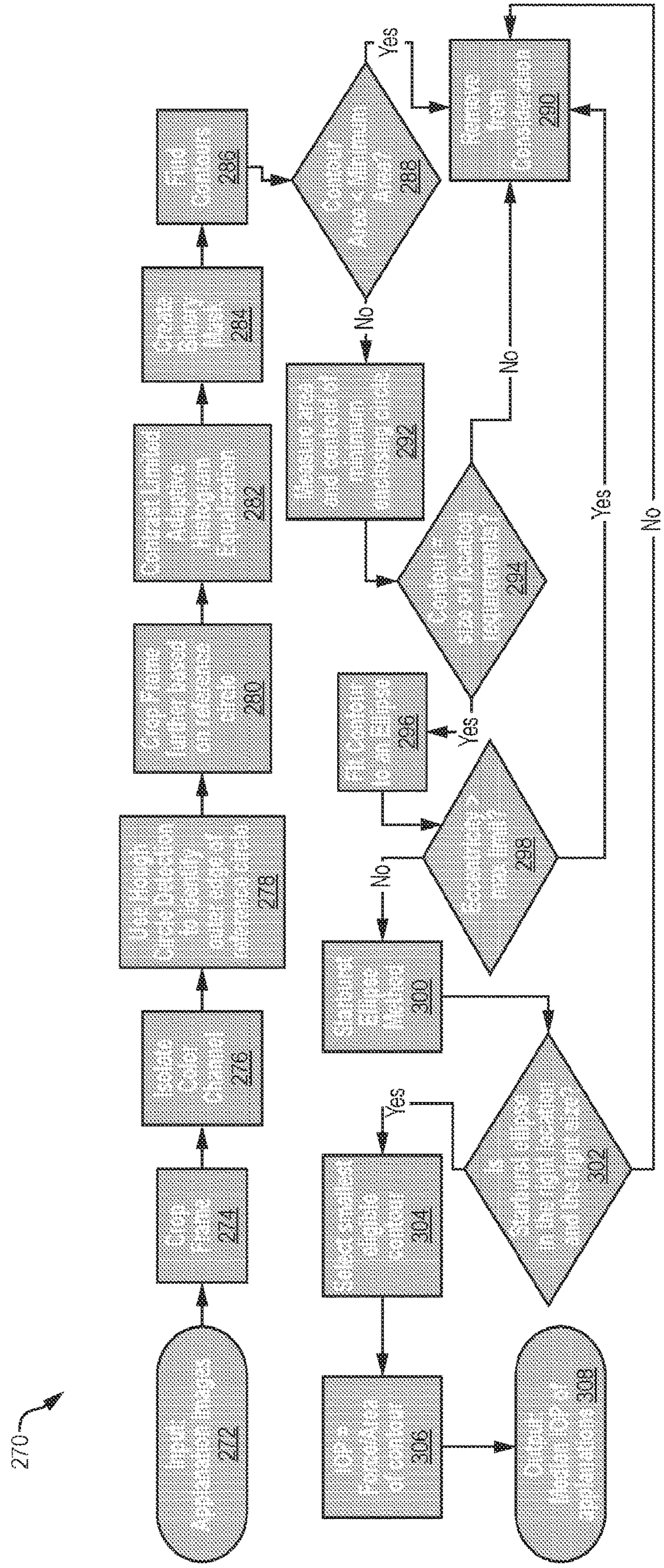
FIG. 6 is a flowchart illustrating one embodiment of an algorithm for use as part of an applanation device.

FIG. 6 is a flowchart illustrating one embodiment of an algorithm 270 for use as part of an applanation device, such as the devices 10, 110, 210. The algorithm 270 is configured to use various known image-processing routines to process the image data and calculate the intraocular pressure. Exemplary image processing routines include edge detection, blob detection, Hough circle detection, contrast limited adaptive histogram equalization, starburst, and the like. The input information is illustrated as the plurality of applanation images or video frames captured by the image-capturing system 250 in FIG. 5. The recording of the images or videos can be continuous, and thus can be considered a continuous IOP reading. As a result, both outflow facility and ocular pulse amplitude, which represents IOP fluctuations that result from the pulse, can be measured, providing tonography and tonometry benefits. Accordingly, devices 10, 110, 210 of the present disclosure are able to obtain objective IOP measurements in a consistent, accurate, and non-invasive way, while also allowing for the ability to make tonographic measurements and/or outflow facility measurements.

The algorithm 270 can begin by having applanation images inputted, as shown at input action 272. The algorithm 270 can be configured to crop each image or frame, as shown at crop action 274, for instance to get rid of dead space on left and/or right edges of the image, isolate the color channels, as shown at isolate action 276, and use Hough Circle Detection to identify the outer edge of the reference circle, as shown at detection action 278. Hough Circle Detection is described in greater detail at https://docs.opencv.org/4.x/dd/dla/group_imgproc_feature.html #ga47849c3be0d0406ad3c a45db65a25d2d, the content of which is incorporated by reference herein in its entirety. In some embodiments, the use of Hough Circle Detection can entail, for every fifth frame, identifying a prism edge using Hough Circle Detection. The image can be further cropped, at crop action 280, based on a last prism edge found, such as the edge of the reference circle.

The contrast of each image can be adjusted, as accounted for at contrast action 282, for example using Contrast Limited Adaptive Histogram Equalization, which is described in greater detail at https://docs.opencv.org/3.4/d6/db6/classcv_1_1CLAHE.html, the content of which is incorporated by reference herein in its entirety. A binary mask can then be created from each image, as shown at mask action 284, for example by thresholding the frame. Further, known image-processing routines can be used to locate contours in each frame, as indicated by finding action 286, including techniques described in greater detail at https://docs.opencv.org/3.4/d3/dc0/group_imgproc_shape.html #ga17ed9f5d79ae97bd4c7cf 18403e1689a, the content of which is incorporated by reference herein in its entirety. After contours are located, a contour evaluation action, as shown by evaluation action 288, can be performed. Any contours that are smaller than a designated minimum area can be removed from consideration, as designated by action 290. As provided for herein, any removal of contours from consideration, or more generally removal of images from the plurality of images captured by the image-capturing system (e.g., the image capturing device 250), can be done to speed up processing time by eliminating contours that are determined to not be applanations.

For each remaining contour, the algorithm 270 can measure the area and centroid of the minimum enclosing circle, as shown by measuring action 292, for example by using the techniques described at https://docs.opencv.org/3.4/d3/dc0/group_imgproc_shape.html #ga8ce13c24081bbc7151e9 326f412190f1, the content of which is incorporated by reference herein in its entirety. A contour size and location evaluation action can occur, as shown by evaluation action 294. If the contour does not meet certain size and/or location requirements (i.e., located inside of the reference circle and/or smaller than the reference circle), the contour can be removed from consideration, as designated again by action 290. The remaining contours can each be fit to an ellipse, as shown by fitting action 296, and eccentricity can be calculated in view of the same. Fitting the contour of an ellipse can be performed using techniques described at https://docs.opencv.org/3.4/d3/dc0/group_imgproc_shape.html #gaf259efaad93098103d6c2 7b9e4900ffa, the content of which is incorporated by reference herein in its entirety. An eccentricity evaluation can be performed as shown by evaluation action 298. If the eccentricity is above a designated maximum limit, the respective contour can be removed from consideration, as designated again by action 290.

The algorithm 270 can then approximate each contour as an ellipse, for example using the starburst method as shown by approximate ellipse action 300 (labeled as starburst method, but other methods of approximating each contour as an ellipse can be possible). More particularly, this can include starting at a distance slightly below an expected ellipse radius and then stepping out radially in evenly-spaced directions (e.g., 20 evenly-spaced directions) until a contour mask is reached. The smallest contour ellipse in each frame can be selected. The ellipse can then be fit to a consecutive set of points (e.g., a consecutive set of 15 points). The best ellipse can then be selected based on parameters such as small size and/or low eccentricity. Evaluation can then be performed to determine whether the identified starburst ellipse is in the right location and is the right size, as shown by evaluation action 302. If not, it can be removed from consideration, as designated once again by action 290.

After analyzing all contours in the frame, if there is more than one eligible contour left, the smallest one can be selected, as shown by selection action 304. Alternatively, if no good contours are identified, a list detailing why each contour failed can be outputted (not shown in flowchart, but stems from evaluation action 302). The selected contour ellipse represents the inner circle or the applanation surface and the area of said ellipse is measured. The IOP can then be calculated, as shown by calculation action 306. The calculation can be based on an area of applanation, and can be added to a buffer of applanations. More particularly, in view of a diameter of the prism edge, typically in millimeters, being known, and a constant force applied by the tonometer also being known, the applanation area in pixels can be converted to a pressure in mmHg. In some embodiments, the IOP calculation can be performed using the Imbert-Fick principle, which states that the IOP equals the force applied divided by the area of the applanation surface. In other embodiments, the algorithm 270 can be configured to calculate the applanation mire diameter using a machine learning and/or deep learning approach. For example, the algorithm 270 can be trained to identify relevant physical features indicative of an applanation mire using a known dataset.

In instances in which applanation is not found in a frame, an applanation buffer can be reviewed. For each applanation, if a length of the applanation buffer does not meet a minimum length requirement, the applanation can be removed from consideration, similar to the designated action 290 for other aspects of the algorithm 270. Likewise, for each applanation, if the length of the applanation buffer meets the minimum length requirement, the first three (3) frames from the applanation buffer can be removed, as these are likely less accurate. Subsequently, a minimum pressure, a maximum pressure, and a mean pressure can be calculated of the remaining applanation buffer(s). If the maximum pressure is greater than the product of the mean pressure and a scaling factor, the applanation can be removed and the maximum pressure and mean pressure can be recalculated. This can be repeated until the maximum pressure is less than the product of the mean pressure and scaling factor. If the minimum pressure is less than the mean pressure divided by a scaling factor, the applanation can be removed and the minimum pressure and mean pressure can be recalculated. This can be repeated until the minimum pressure is greater than the mean pressure divided by the scaling factor. Although these actions are not explicitly illustrated related to calculation action 306 are not separately illustrated as steps or actions of the algorithm 270, a person skilled in the art will appreciate these action can be included as part of the algorithm 270 and/or that other actions can be performed to calculate IOP in view of the information provided by the inputted applanation images that occurred at action 272. Once completed, the data of any remaining good applanations can be saved. Further, after all frames are processed—frames with and without applanations found in the frame—a median pressure of good applanations can be calculated, which can be outputted as the IOP, as shown by output action 308.

Figure 7:
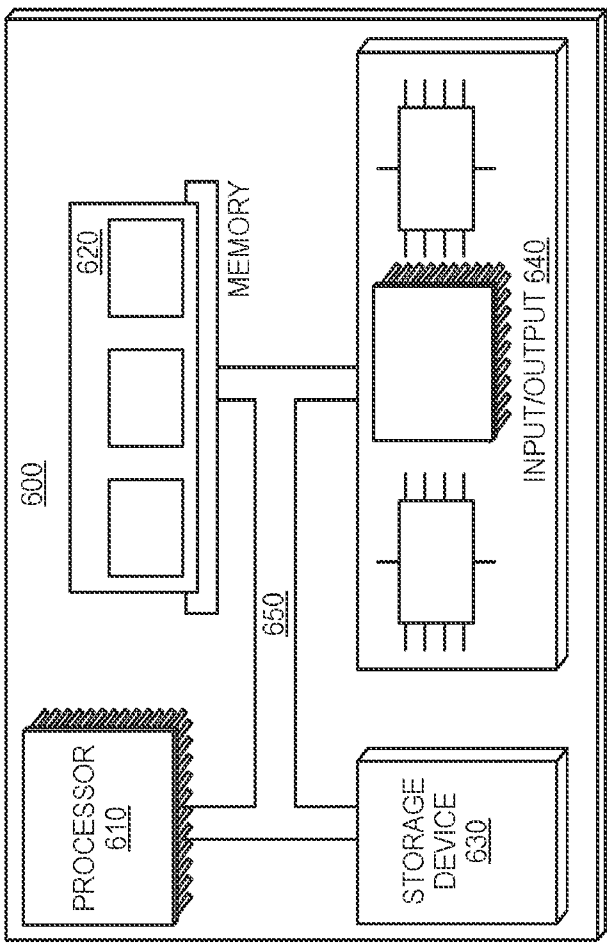
FIG. 7 is a schematic block diagram of one exemplary embodiment of a computer system for use in conjunction with the present disclosures.

FIG. 7 provides for one non-limiting example of a computer system 600 upon which actions provided for in the present disclosure can be built, performed, trained, etc. The system 600 can include a processor 610, a memory 620, a storage device 630, and an input/output device 640. Each of the components 610, 620, 630, and 640 can be interconnected, for example, using a system bus 650. The processor 610 can be capable of processing instructions for execution within the system 600. The processor 610 can be a single-threaded processor, a multi-threaded processor, or similar device. The processor 610 can be capable of processing instructions stored in the memory 620 or on the storage device 630. The processor 610 may execute operations such as processing image data by way of an algorithm (e.g., the algorithm 270), among other features described in conjunction with the present disclosure.

The memory 620 can store information within the system 600. In some implementations, the memory 620 can be a computer-readable medium. The memory 620 can, for example, be a volatile memory unit or a non-volatile memory unit. In some implementations, the memory 620 can store information related to image processing, among other information.

The storage device 630 can be capable of providing mass storage for the system 900. In some implementations, the storage device 630 can be a non-transitory computer-readable medium. The storage device 630 can include, for example, a hard disk device, an optical disk device, a solid-date drive, a flash drive, magnetic tape, or some other large capacity storage device. The storage device 630 may alternatively be a cloud storage device, e.g., a logical storage device including multiple physical storage devices distributed on a network and accessed using a network. In some implementations, the information stored on the memory 620 can also or instead be stored on the storage device 630.

The input/output device 640 can provide input/output operations for the system 900. In some implementations, the input/output device 640 can include one or more of network interface devices (e.g., an Ethernet card), a serial communication device (e.g., an RS-232 10 port), and/or a wireless interface device (e.g., a short-range wireless communication device, an 802.11 card, a 3G wireless modem, or a 4G wireless modem). In some implementations, the input/output device 640 can include driver devices configured to receive input data and send output data to other input/output devices, e.g., a keyboard, a printer, and display devices (such as the GUI 12). In some implementations, mobile computing devices, mobile communication devices, and other devices can be used.

In some implementations, the system 600 can be a microcontroller. A microcontroller is a device that contains multiple elements of a computer system in a single electronics package. For example, the single electronics package could contain the processor 610, the memory 620, the storage device 630, and input/output devices 640.

Although an example processing system has been described above, implementations of the subject matter and the functional operations described above can be implemented in other types of digital electronic circuitry, or in computer software, firmware, and/or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine-readable storage device, a machine-readable storage substrate, a memory device, a composition of matter effecting a machine readable propagated signal, or a combination of one or more of them.

Various embodiments of the present disclosure may be implemented at least in part in any conventional computer programming language. For example, some embodiments may be implemented in a procedural programming language (e.g., "C"), or in an object-oriented programming language (e.g., "C++"). Other embodiments of the invention may be implemented as a pre-configured, stand-along hardware element and/or as preprogrammed hardware elements (e.g., application specific integrated circuits, FPGAs, and digital signal processors), or other related components.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Such implementation may include a series of computer instructions fixed either on a tangible, non-transitory medium, such as a computer readable medium. The series of computer instructions can embody all or part of the functionality previously described herein with respect to the system. Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud computing model. Of course, some embodiments of the present disclosure may be implemented as a combination of both software (e.g., a computer program product) and hardware. Still other embodiments of the present disclosure are implemented as entirely hardware, or entirely software.

Examples of the above-described embodiments can include the following:

1. An applanation device, comprising:
   - a housing forming an internal cavity, the housing having an applanator access opening formed in an outer wall thereof, the applanator access opening providing access between the internal cavity and an outside environment;
   - an applanator disposed in the internal cavity of the housing, the applanator having a distal tip configured to pass into and through the applanator access opening to apply a force to an eye of a subject located in the outside environment;
   - an image-capturing system disposed in the internal cavity of the housing and configured to capture a plurality of applanation images of the eye; and
   - a controller configured to receive the plurality of applanation images captured by the image-capturing system and determine intraocular pressure in the eye based on the captured plurality of applanation images.

2. The applanation device of example 1, wherein the force applied to the eye by the distal tip of the applanator is a constant force for a duration of time during which the plurality of applanation images of the eye are captured.
3. The applanation device of example 1 or example 2, wherein the applanator further comprises:
   a lever arm having a first end, a second end, and a fulcrum disposed therebetween; and
   a counterweight disposed on a second side of the fulcrum, more proximate to the second end than the first end,
   wherein the distal tip is disposed on a first side of the fulcrum, more proximate to the first end than the second end.
4. The applanation device of example 3, further comprising:
   a constant force spring coupled to the lever arm and configured such that the force applied to the eye by the distal tip of the applanator is a constant force.
5. The applanation device of any of examples 1 to 4, further comprising:
   a sensor configured to measure the force applied by the distal tip to the eye and communicate the measured force to the controller.
6. The applanation device of any of examples 1 to 5, further comprising:
   a force-adjustment mechanism associated with the housing, the force-adjustment mechanism being in communication with the applanator and the force-adjustment mechanism being configured to change an amount of the force being applied to the eye.
7. The applanation device of any of examples 1 to 6, wherein the controller is further configured to be in communication with the applanator such that the controller can direct a change in an amount of the force being applied to the eye.
8. The applanation device of any of examples 1 to 7, wherein the distal tip is conically-shaped and conformable.
9. The applanation device of any of examples 1 to 8, wherein the distal tip is monolithic.
10. The applanation device of any of examples 1 to 9, wherein the image-capturing system comprises at least one camera.
11. The applanation device of any of examples 1 to 10, further comprising:
   at least one illumination source disposed in the housing and configured to supply light to the distal tip.
12. The applanation device of any of examples 1 to 11,
   wherein the controller is configured to identify an outer reference circle that is representative of a circumference of the distal tip and an inner circle that is representative of an applanation mire such that a surface area of the applanation mire can be determined, and
   wherein the intraocular pressure of the eye is determined based on the determined surface area of the applanation mire and an amount of the force applied to the eye.
13. The applanation device of any of examples 1 to 12, wherein the controller is configured to remove from consideration one or more images of the plurality of applanation images captured by the image-capturing system to speed up processing time to determine intraocular pressure in the eye.
14. The applanation device of example 13, wherein the controller is configured to remove from consideration one or more images of the plurality of applanation images captured by the image-capturing system based on at least one of:
   one or more identified contours of the one or more images; or
   one or more starburst ellipses approximated from the one or more images.
15. The applanation device of example 14,
   wherein removal from consideration one or more images of the plurality of applanation images captured by the image-capturing system is based at least on the one or more identified contours of the one or more images, and
   wherein parameters of the contours on which such removal is based comprise at least one of:
      a contour area;
      a contour size;
      a contour location; or
      an eccentricity of the contour after fit to an ellipse.
16. The applanation device of any of examples 1 to 15, wherein the distal tip comprises one or more fiducial markings thereon to provide reference points for determining a reference distance upon which the controller can rely upon to calculate intraocular pressure.
17. The applanation device of any of examples 1 to 16, wherein the housing provides for the applanation device to be a portable, handheld applanation device.
18. The applanation device of any of examples 1 to 17, further comprising:
   a power source disposed in the internal cavity of the housing, the power source providing power to at least one of the image-capturing system or the controller.
19. The applanation device of any of examples 1 to 18, wherein the controller is disposed in the housing.
20. The applanation device of any of examples 1 to 19, wherein the controller is disposed outside of the housing.
21. The applanation device of example 20, wherein the controller is provided as part of at least one of a computer or smartphone.
22. The applanation device of any of examples 1 to 21, wherein the applanation device is configured to measure both intraocular pressure and an outflow facility of an eye.
23. The applanation device of any of examples 1 to 22, wherein the applanation device is configured to be used both when the subject is in a supine position and when the subject is in an upright position.
24. A method of measuring at least one of intraocular pressure in an eye or an outflow facility of an eye, comprising:
   placing a distal tip of an applanator on a surface of an eye of a subject to cause a fixed force to be applied to the eye;
   capturing a plurality of applanation images of the eye while the fixed force is applied to the eye; and
   operating a processor to use information from the applanation images and the fixed force to determine at least one of intraocular pressure in the eye or an outflow facility of the eye.
25. The method of example 24, wherein the applanator further comprises:
   a lever arm having a first end, a second end, and a fulcrum disposed therebetween; and a counterweight disposed on a second side of the fulcrum, more proximate to the second end than the first end, wherein the distal tip is disposed on a first side of the fulcrum, more proximate to the first end than the second end, and wherein the counterweight supplies a counter fixed force to enable application of the fixed force to the eye.

26. The method of example 24 or example 25, further comprising:

measuring a value of the fixed force; and communicating that measured value of the fixed force to the processor.

27. The method of any of examples 24 to 26, further comprising:

adjusting a value of the fixed force to a prescribed value.

28. The method of example 27, wherein adjusting a value of the fixed force to a prescribed value further comprises causing the distal tip to apply the fixed force at a preset value such that the preset value becomes the adjusted value.

29. The method of example 27, wherein adjusting a value of the fixed force to a prescribed value further comprises operating one or more controls associated with the applanator to adjust the value of the fixed force across a plurality of values.

30. The method of any of examples 24 to 29 further comprising:

operating at least one of the processor or a separate processor to identify from the plurality of applanation images an outer reference circle that is representative of a circumference of the distal tip of the applanator and an inner circle that is representative of an applanation mire to determine a surface area of the applanation mire;

wherein the information from the applanation images used to determine the intraocular pressure in the eye comprises the surface area of the applanation mire.

31. The method of example 30, further comprises using one or more fiducial markings on the distal tip of the applanator to provide reference points used in conjunction with the information from the applanation images to determine the intraocular pressure in the eye.

32. The method of any of examples 24 to 31, further comprising:

operating at least one of the processor or a separate processor to remove from consideration one or more images of the plurality of applanation images captured by the image-capturing system to speed up processing time to determine intraocular pressure in the eye.

33. The method of example 32, wherein operating at least one of the processor or a separate processor to remove from consideration one or more images of the plurality of applanation images captured by the image-capturing system further comprises removing the one or more images from consideration based on at least one of:

one or more identified contours of the one or more images; or one or more starburst ellipses approximated from the one or more images.

34. The method of example 33, wherein removing the one or more images from consideration is based at least on the one or more identified contours of the one or more images, and wherein parameters of the contours on which such removal is based comprise at least one of:

a contour area;

a contour size;

a contour location; or an eccentricity of the contour after fit to an ellipse.

35. The method of any of examples 24 to 34, wherein the applanator is disposed within a housing of a portable, handheld applanation device.

36. The method of any of examples 24 to 35, wherein both intraocular pressure in the eye and the outflow facility of the eye are measured during the same procedure.

37. The method of any of examples 24 to 36, wherein the subject is able to be in either a supine position or an upright position when placing the distal tip of the applanator on the surface of the eye of the subject and when capturing the plurality of applanation images of the eye while the fixed force is applied to the eye.

One skilled in the art will appreciate further features and advantages of the disclosure based on the above-described embodiments. Accordingly, the disclosure is not to be limited by what has been particularly shown and described, except as indicated by the appended claims. All publications and references cited herein are expressly incorporated herein by reference in their entirety.

What is claimed is:

1. An applanation device, comprising:

a housing forming an internal cavity, the housing having an applanator access opening formed in an outer wall thereof, the applanator access opening providing access between the internal cavity and an outside environment;

an applanator disposed in the internal cavity of the housing, the applanator having a distal tip configured to pass into and through the applanator access opening to apply a force to an eye of a subject located in the outside environment;

an image-capturing system disposed in the internal cavity of the housing and configured to capture a plurality of applanation images of the eye; and a controller configured to:

receive the plurality of applanation images captured by the image-capturing system;

identify an outer reference circle that is representative of a circumference of the distal tip and a contour in the plurality of applanation images;

fit the contour to an ellipse that is representative of an applanation mire such that a surface area of the applanation mire is determined; and determine intraocular pressure in the eye based on the determined surface area of the applanation mire and an amount of the force applied to the eye.

2. The applanation device of claim 1, wherein the force applied to the eye by the distal tip of the applanator is a constant force for a duration of time during which the plurality of applanation images of the eye are captured.

3. The applanation device of claim 1, wherein the applanator further comprises:

a lever arm having a first end, a second end, and a fulcrum disposed therebetween; and a counterweight disposed on a second side of the fulcrum, more proximate to the second end than the first end, wherein the distal tip is disposed on a first side of the fulcrum, more proximate to the first end than the second end.

4. The applanation device of claim 3, further comprising:

a constant force spring coupled to the lever arm and configured such that the force applied to the eye by the distal tip of the applanator is a constant force.

5. The applanation device of claim 1, further comprising:

a force-adjustment mechanism associated with the housing, the force-adjustment mechanism being in communication with the applanator and the force-adjustment mechanism being configured to change an amount of the force being applied to the eye.

6. The applanation device of claim 1, wherein the controller is further configured to be in communication with the applanator such that the controller directs a change in an amount of the force being applied to the eye.

7. The applanation device of claim 1, wherein the controller is configured to remove from consideration one or more images of the plurality of applanation images captured by the image-capturing system to speed up processing time to determine intraocular pressure in the eye.

8. The applanation device of claim 7, wherein the controller is configured to remove from consideration one or more images of the plurality of applanation images captured by the image-capturing system based on at least one of:

one or more identified contours of the one or more images; or one or more starburst ellipses approximated from the one or more images.

9. The applanation device of claim 1, wherein the housing provides for the applanation device to be a portable, handheld applanation device.

10. A method of measuring at least one of intraocular pressure in an eye or an outflow facility of an eye, comprising:

placing a distal tip of an applanator on a surface of an eye of a subject to cause a fixed force to be applied to the eye;

capturing a plurality of applanation images of the eye while the fixed force is applied to the eye;

identifying an outer reference circle that is representative of a circumference of the distal tip and a contour in the plurality of applanation images;

fitting the contour to an ellipse that is representative of an applanation mire such that a surface area of the applanation mire is determined; and operating a processor to determine the surface area of the applanation mire and use the surface area of the applanation mire from the applanation images and the fixed force to determine at least one of intraocular pressure in the eye or an outflow facility of the eye.

11. The method of claim 10, wherein the applanator further comprises:

a lever arm having a first end, a second end, and a fulcrum disposed therebetween; and a counterweight disposed on a second side of the fulcrum, more proximate to the second end than the first end, wherein the distal tip is disposed on a first side of the fulcrum, more proximate to the first end than the second end, and wherein the counterweight supplies a counter fixed force to enable application of the fixed force to the eye.

12. The method of claim 10, further comprising:

measuring a value of the fixed force; and communicating that measured value of the fixed force to the processor.

13. The method of claim 10, further comprising:

adjusting a value of the fixed force to a prescribed value.

14. The method of claim 13, wherein adjusting a value of the fixed force to a prescribed value further comprises causing the distal tip to apply the fixed force at a preset value such that the preset value becomes the adjusted value.

15. The method of claim 13, wherein adjusting a value of the fixed force to a prescribed value further comprises operating one or more controls associated with the applanator to adjust the value of the fixed force across a plurality of values.

16. The method of claim 10, further comprising:

operating at least one of the processor or a separate processor to remove from consideration one or more images of the plurality of applanation images captured by the image-capturing system to speed up processing time to determine intraocular pressure in the eye.

17. The method of claim 16, wherein operating at least one of the processor or a separate processor to remove from consideration one or more images of the plurality of applanation images captured by the image-capturing system further comprises removing the one or more images from consideration based on at least one of:

one or more identified contours of the one or more images; or one or more starburst ellipses approximated from the one or more images.

18. The method of claim 17, wherein removing the one or more images from consideration is based at least on the one or more identified contours of the one or more images, and wherein parameters of the contours on which such removal is based comprises at least of:

a contour area;

a contour size;

a contour location; or an eccentricity of the contour after fit to an ellipse.

* * * * *